(12) United States Patent
Cosentino et al.

(10) Patent No.: US 7,008,292 B2
(45) Date of Patent: Mar. 7, 2006

(54) STRUCTURE FOR SUPPORTING BODY PARTS OF THE HUMAN BODY

(75) Inventors: Lorenzo Cosentino, Caselle di Sommacampagna (IT); Gabriella Torregrossa, Verona (IT); Gianluca Castellarin, Verona (IT); Stefano Bucci, Verona (IT)

(73) Assignee: Luca Nardi, S. Bonifacio (IT)

( * ) Notice: Subject to any disclaimer, the term of this patent is extended or adjusted under 35 U.S.C. 154(b) by 0 days.

(21) Appl. No.: 10/275,657

(22) PCT Filed: May 11, 2001

(86) PCT No.: PCT/IT01/00230

§ 371 (c)(1),
(2), (4) Date: Mar. 7, 2003

(87) PCT Pub. No.: WO01/85072

PCT Pub. Date: Nov. 15, 2001

(65) Prior Publication Data

US 2003/0171068 A1 Sep. 11, 2003

(30) Foreign Application Priority Data

May 11, 2000 (IT) .................................. RM2000A0253
May 10, 2001 (IT) .................................. RM2001A0245

(51) Int. Cl.
*A41C 3/00* (2006.01)
*A41D 13/00* (2006.01)

(52) U.S. Cl. ............................................ 450/155; 2/92
(58) Field of Classification Search ........................ 2/44, 2/92; 450/155, 1, 30–33, 7–11, 14–18; 602/19, 602/2, 60, 61, 67, 70; 128/99.1, 96.1, 100.1, 128/101.1, 106.1, 107.1, 109.1, 869, 870, 128/873, 874, 875, 876
See application file for complete search history.

(56) References Cited

U.S. PATENT DOCUMENTS

| | | | | |
|---|---|---|---|---|
| 407,341 A | * | 7/1889 | Ferris | 450/155 |
| 664,214 A | | 12/1900 | Golden | |
| 912,769 A | * | 2/1909 | Anderson | 450/155 |
| 1,110,226 A | * | 9/1914 | Payne | 450/155 |
| 2,023,707 A | * | 12/1935 | Rosenfeld | 450/155 |
| 2,250,807 A | * | 7/1941 | Lunney | 450/155 |
| 2,345,760 A | * | 4/1944 | Lunney | 450/155 |
| 2,743,449 A | * | 5/1956 | Sheldon | 450/155 |
| 3,273,563 A | | 9/1966 | Bonang | |
| 4,746,318 A | * | 5/1988 | Moyer | 450/155 |
| 4,789,372 A | * | 12/1988 | Wicks | 450/155 |
| 4,822,317 A | * | 4/1989 | Wimmer | 450/155 X |
| 4,836,824 A | | 6/1989 | Seering et al. | |
| 4,867,145 A | * | 9/1989 | Goth | 128/99.1 X |
| 4,952,192 A | | 8/1990 | Burke | |
| 5,060,639 A | * | 10/1991 | Marcus | 128/101.1 X |
| 5,532,681 A | * | 7/1996 | Peters et al. | 340/573 |
| 5,915,531 A | | 6/1999 | Hilpert et al. | |
| 5,928,059 A | * | 7/1999 | Wicks | 450/155 |
| 6,023,632 A | * | 2/2000 | Wilk | 600/407 |
| 6,159,070 A | * | 12/2000 | Schwartz et al. | 450/155 |
| 6,200,279 B1 | * | 3/2001 | Paltieli | 600/588 |

FOREIGN PATENT DOCUMENTS

| | | |
|---|---|---|
| CA | 2 029 655 A | 5/1992 |
| DE | 36 28 995 A | 3/1988 |
| GB | 2 260 270 A | 4/1993 |
| WO | WO 96/29898 A1 | 10/1996 |

OTHER PUBLICATIONS

International Search Report WO 01/85072 Nov. 15, 2001.

* cited by examiner

*Primary Examiner*—Gloria M. Hale
(74) *Attorney, Agent, or Firm*—Birch, Stewart, Kolasch & Birch LLP

(57) ABSTRACT

A dorsal bodice and a structured abdominal suspension strap adapted to contain and support the belly, the abdominal suspension strap being adjustably connected to the dorsal bodice by connecting straps and connectors for adjusting the tension of the connecting straps.

11 Claims, 11 Drawing Sheets

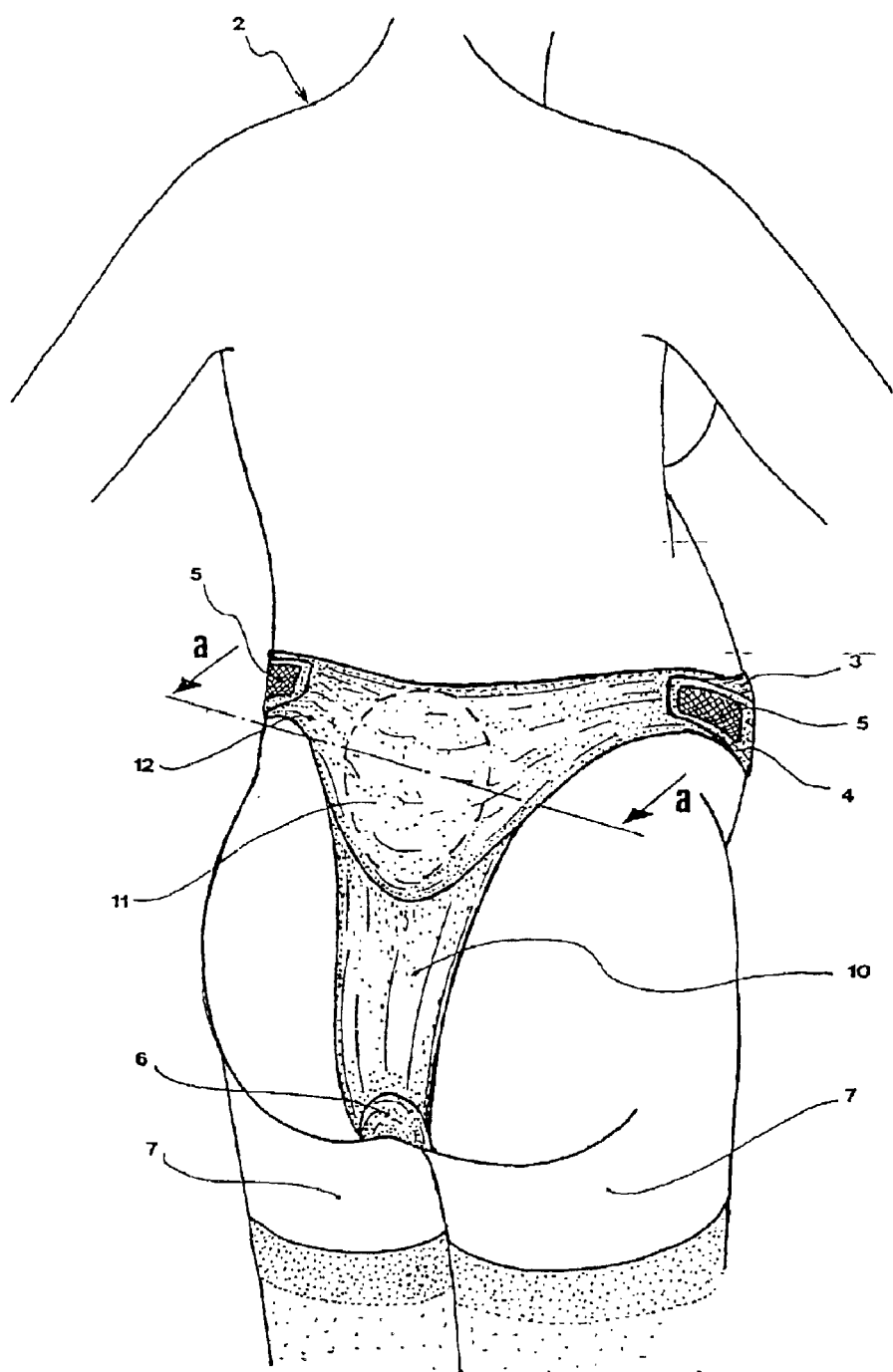
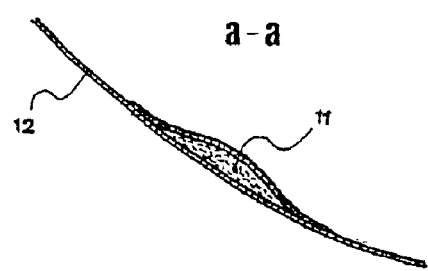
fig.2
fig.2a

STRUCTURE FOR SUPPORTING BODY PARTS OF THE HUMAN BODY

BACKGROUND OF THE INVENTION

This application is the national phase under 35 U.S.C. § 371 of PCT International Application No. PCT/IT01/00230 which has an International filing date of May 11, 2001, which designated the United States of America.

FIELD OF THE INVENTION

The present invention is directed to an abdominal suspension system for pregnant women who are subjected, due to the increase in dimensions and weight of the uterus, to lumbar and pelvic pain associated with the increased lordosis with the entailed overloading of the vertebrae and related intervertebral disks, particularly at the first and fifth lumbar sacral vertebrae due both to the increased tilt of the lumbosacral angle and to the frontal stretching of the pubic symphysis by the uterus. In particular, the present invention is concerned with a multiple strap-structured protector for supporting the pregnant abdomen through an abdominal suspensor tensionally joined to a top dorsal bodice, loosely enveloping the back and the shoulders.

BACKGROUND OF THE INVENTION

The substantial weight increase in pregnancy, mainly occurring over the latter 20 gestational weeks is known. Incidentally, in pregnancy the weight increase may often reach about 15 Kg and over, 70% thereof occurring over the latter 20 gestational weeks, and being largely due to water retention and to an increase of the fat reserve.

It is also known that in pregnancy the joints, the ligaments and the musculotendinous structure of the pelvis and of the spine are particularly lax. The increased joint laxity and elasticity allows an easier adaptation of the pelvic shape to the fetus.

During pregnancy a relaxation of the ligament and tendon system, following changes in the hormonal state, among which a sensible increase in the level of the progesterone hormone, is observed. The relaxation affects the whole body, yet it becomes particularly apparent at the sacroiliac joints and at the pubic symphysis, with a greater stretching of the ligaments, and therefore with pain derived from the stress exerted by the growing/swelling uterus. At the vertebral level, particularly in the highly mobile lumbar tract, the ligamentous laxity may foster the presence of microstrains, in particular against the articular facets, responsible for low back pain. Moreover, at the lower lumbar vertebrae and at the lumbosacral passage, where, following the enhanced lumbar lordosis posture, the compressive stress onto the vertebral bodies and the vertebral disks concentrate, a greater rate of disk protrusions occurs. The latter are also fostered by a greater laxity of the posterior longitudinal ligament, with the entailed compression of the intrarachidean nerve plexus creating lower back pain.

The relaxation of the ligament system, typical of the pregnant state, causes a certain spreading apart of the pelvic bones during pregnancy. In particular, the diastasis of the pubic symphysis causes a symptomatology represented by pubic and lumbosacral pain which is enhanced by motion, making walking problematic.

Such lumbar and pelvis algetic symptomatology is very frequent in pregnancy, with an incidence that tends to increase in the course thereof, when uterine volume and weight are mostly increased, until reaching an apex around the end of the eighth month, when approximately three women out of four intensely suffer therefrom.

The etiopathogenesis of such pain is certainly multifactorial. However, in the most significant and recent studies and experimentation of the applicant the 'mechanical' factor was specifically investigated. The 'mechanical' factor is relevant in the course of pregnancy. In fact, following the increased dimensions and weight of the uterus and the relaxation of the abdominal wall, the center of gravity gradually tends to shift forwards, causing accentuated lumbar lordosis. This entails important modifications of the spine morphology, comprising, in fact, the accentuation of the lumbar lordosis physiology, a backward shifting of the sacrum causing a progressive verticalization of the lumbosacral angle, a stretching of the sacroiliac joints, and finally a stretching against the pubic symphysis. At times, also sciatic neuralgia from herniated disc-deriving discoradicular compression is developed. To compensate for the above, the shoulders, the neck and the head are brought backwards and the pelvis is slightly rotated onto the femurs.

These postural modifications induce pregnant women to assume a typical waddling gait, with the entailed overloading of the vertebrae and of the related intervertebral disks, particularly at the fifth lumbar and first sacral vertebrae, following the increased tilt of the lumbosacral angle.

Various different abdominal suspensors capable of relieving the pain, concomitantly lightening the sensation of abdominal burden both during walking and while standing have long been advanced in the art. Such an effect also depends on the reduction of the stretching of the muscoloskeletal ligamentous and uterine systems, often causing pelvic and inguinal pain.

Abdominal suspensors having an abdomen-pelvic supporting strap anchored merely to the lumbar region, though constituting a valuable support for the abdominal wall of a woman during pregnancy, grow ineffective as the latter progresses due to the conspicuous increase of a pregnant uterus. Also the abdominal suspensors known in the art generally discharge the weight onto the lumbar region. Hence, the applicant has faced the problem in its entirety, with the precise object of providing an abdominal suspension system and a multimember structural-type protector capable of providing a construction which features functional and preventive therapy for overcoming the drawbacks mentioned with reference to the known art.

In fact, the advantages of the protector hereinafter disclosed, with an original solution, provide a substantial aid to the pregnant woman during the entire pregnancy.

SUMMARY OF THE INVENTION

Hence, an object of the present invention is to provide a method capable of:

supporting the abdomen on one hand and protecting the spine on the other hand during the entire pregnancy;

providing to the pregnant woman an immediate and continual feeling of relief, support and protection of the abdomen;

improving the general symptomatology through a drastic reduction of the gravitational load on the belly;

substantially limiting the load onto the vertebral column and replacing the activity of the abdominal muscles by externally supporting the abdomen;

abating the risk of an onset of discopathies with associated painful sciatic neuralgiae;

allowing the pregnant woman to maintain a satisfactory postural musculoskeletal balance;

allowing the pregnant woman to avoid functional handicaps and to normally carry out her everyday life activities without the limitations often associated with algetic symptomatology;

aiding the venous circulation and above all preventing the vascular complication inherent to pregnancy.

Another object of the present invention is to provide a dorsal and abdominal protector of simplified implementation, utmost wearability and sturdiness for its task of tensioned suspensor and providing a faultless protection.

A further object of the present invention is to adjust the wearability and the support tensioning following an increase in the dimensions and weight of the abdomen due to the expanding of the uterus with adjusting and locking means handy and ready for use.

Hence, the task underlying the present invention is to provide an adjustable abdominal suspension system and to implement a structured protector whereby the partially indicated drawbacks and disadvantages entailed in the traditional embodiments advanced by the art may generally be eliminated. Moreover, the attainment of these objects and others is ensured by carrying out the following protective steps:

supporting the abdomen of a pregnant woman with an abdominal suspensor having multiple back straps enveloping the bottom area of the lumbar spine and continuing with a tensioned union to a top dorsal bodice, loosely enveloping the shoulders;

protecting the spine by supporting the weight of the abdomen on both shoulders and bringing the abdomen upwards to push it back in order to activate the backing off of the body barycenter with a reduction of the tilt of the lumbosacral angle to relieve the stress on the sacroiliac joints;

lightening the burden on the spine by shifting the weight of the abdomen onto the shoulder girdle by means of the adjustable tensioning of the anterolateral straps at the top dorsal bodice in order to substitute for the muscular strata of the abdominal wall;

adopting a panty-shaped abdominal suspensor in order to avoid the compressive crushing in the inguinal area at the saphenous femoral outlet and using a low-elastic enveloping composite fabric, and also pre-setting the former elastic stocking fastening means suitably graduated to the elastocompressive action as a restraining and preventive therapy in the presence of venous insufficiency;

adjusting function of the restraining width of the suprapubic strap in the course of the gestational months and maintaining the normal curvature in the lumbar area of the spine during pregnancy by means of the pressing action exerted by pads modelled to the applied body area and capable of stabilizing the vertebral segment in achieving the correct curvature thereof, and avoiding a congenital alteration of the spine and muscle disorders which cause pain and vertigo to the pregnant woman;

pre-setting conductive yarn into the fabric of the abdominal suspensor and of the dorsal bodice for providing electrical continuity and communication with electromedical comfort ware and to electronic foetal monitoring sensing devices for sensing regular fetal in uterus development.

These tasks are attained by a dorsal and abdominal protector for supporting the belly of pregnant women, which includes a dorsal bodice, a strap-structured abdominal suspensor adapted to contain and support the belly, connected thereto; and means for adjusting the tension of these straps.

The method and system, according to the present invention, has an abdominal suspensor of a particular structured composite, utilizing a plurality of straps to form a single product of easy wearability adaptable to variable configurations of the entire abdominal wall and to contiguous bottom portions of muscles at the root of the thighs and pelvis to provide a rearward supporting of the spine and the back-enveloping muscles. Unconstrained portions of the straps of the composite structure of the abdominal suspensor are joined and associated at the free ends thereof with removable means, e.g., adjustable hooks or clasps, or "VELCRO" hook and loop fastener tear-off straps for fastening, or loosening the device to render it variably adaptable in order to regularize and adapt the abdominal suspensor during the entire pregnancy.

According to a further embodiment, the present invention provides in the bottom portion of the pelvis, a back structure removable band for allowing, in an opened position, a normal urine outflow and/or fecal expulsion, and, in a closed position, a steady coupling and prevention and containment of probable and irritating pelvic relaxation during pregnancy.

According to a further embodiment, the front abdominal suspensor is formed by at least one yielding elastic enveloping top strap covering the entire abdomen, by at least one back structured bottom strap supporting the weight of the pregnant abdomen by means of the tensional coupling to the back rear sacrolumbar strap and by the support anchoring to the top dorsal bodice, extending to envelop the entire back of the thoracic vertebrae to share the support of the weight to a wide dorsal surface which projects topwise to completely envelop the shoulders.

According to a further embodiment a bra strap is provided for effecting the removable and adjustable coupling to the dorsal bodice for supporting the weight of the pregnancy-swollen breast by the shoulders and back.

According to a further embodiment the present invention balances several sets of resulting forces by means of the structural union between the abdominal suspensor and the supporting dorsal bodice, thereby burdening the shoulder girdle with substantially the entire weight of the pregnant abdomen discharges. Thus, the abdomen is supported in the upwards direction and pushed rearwards in order to back the body barycenter, thereby promoting a reduction in the tilt of the lumbosacral angle, and relieving the stress on the sacroiliac joints, and entail pain.

According to a further embodiment the method and device provide for fetal monitoring carried out with devices which sense the fetal heart sounds and the prenatal uterine contractions, and the sensed data are transmitted, through the electrical conductivity of the fabric to a control unit associated with a battery generator to activate a display easily accessible to a field of view of a pregnant woman for indicating and informing the doctor of the pregnancy or state of condition. Under border conditions of irregular values the above mentioned electronic foetal monitoring can be transmitted to a radiofrequency installation for communicating the progress attained in treating the pregnancy and recognizing complications for increasing the safety of the pregnant woman and fetus and to timely select suitable therapy.

According to a further embodiment the method allows electrostimulation and/or electromagnetic stimulation and/or ultrasound therapeutic treatments with antalgic and/or aesthetical strengthening effects, suitable for the pregnant state, and to avoid soreness of specific body areas and mobility restrictions.

The structural-type protector of the present invention includes:

an abdominal suspensor structured in multiple front and rear straps with various fabric compositions for different required functions, said straps being bottomwise completed by a panty, in a slightly elastic fabric enveloping the buttocks and the thighs, near the groin, both allowing an adaptability graduated and adjusted according to the gestational month. The straps are fastened, preferably with "VELCRO" hook and loop fastener straps, elastic stockings suitable for elastocompressive action along the legs, etc., as restraining and preventive therapy in the presence of venous insufficiency of the pregnant woman;

a top dorsal bodice manufactured in a backed composite fabric loosely enveloping the shoulders and the dorsal area to about the height level of the lumbar vertebrae, and descending in anterolateral positions with straps shaped for easy adjustable tensional anchoring to the underlying abdominal suspensor in order to form a continuous fabric structure for supporting the pregnant abdomen, the weight of the latter being discharged to the shoulder girdle for relieving the vertebrae and the related intervertebral disks, in particular the fifth lumbar and first sacral vertebrae following the unchanged tilt of the lumbosacral angle;

a bra with an adjustable anchoring and easy removability from the top dorsal bodice, preferably provided with removable connectors on the anterolateral straps;

pocket-shaped inside and outside seats, or inside and outside hook-, buckle- or "VELCRO" hook and loop fastener type connectors for associating with the abdominal suspensor and/or to the dorsal bodice of the pregnant women and electronic fetal monitoring devices and/or therapeutical ware with antalgic and/or strengthening effects;

pads modelled to the body configuration satisfying the needs of therapy and for the prevention of lumbosacral pain in pregnancy in order to prevent motor functional difficulties in the pregnant woman, who should be in the best possible condition carrying out her everyday activities without the known limitations frequently inflicted by the algetic symptomatology.

According to another embodiment, the dorsal and abdominal protector of the present invention has an abdominal suspensor and a dorsal bodice of distinct wearability to be necessarily joined into a single garment by means of known removable anchorings, all operating with a wide adjustment of stable tensional support between the abdominal straps and the bodice portion enveloping the top dorsal end shoulder girdle.

According to a further embodiment, the dorsal and abdominal protector of the present invention has an abdominal suspensor and a dorsal bodice in form of a single garment of joined wearability with anterolateral straps of oversize extension to be rolled up and/or shortened on themselves with buckles. Also, sliding means is provided for a wide tensional support adjustment between the abdominal straps and the dorsal bodice portion enveloping the shoulder girdle.

According to a further embodiment the dorsal and abdominal protector is generally made of textile fabric straps structured with an inner layer which contacts the skin being made of a thin permeable fabric of natural yarn adapted to prevent condensing sweat from contacting the skin.

According to a further embodiment the dorsal and abdominal protector is made of a textile material composition incorporating therein conductive fibers which provide uniform electrical continuity, or in lieu thereof and/or overlapped thereto, optical fibers and/or optical fiber sensors can be incorporated therein.

Said conductive fibers and/or optical fibers and/or optical fiber sensors are advantageously connected to foetal monitoring instrumentation to carry out and control signals carrying in real time information about the foetal heart sounds and prenatal uterine contractions.

According to a further embodiment, at the entry and/or exit sites of the optical fibers from the dorsal and abdominal protector is protected by the textile structure of the abdominal suspensor and/or of the dorsal bodice by means of small rubber disks glued onto the surface of the textile structure itself, in order to eliminate the difficulties connected with the trimming for modelling the straps in presence of optical fibres.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein:

FIG. 2 is a schematic isometric perspective view of the abdominal suspensor shown from the rear with the back strap enveloping the bottom area of the sacral spine and with a vertical inguinal-extending back strap, said view also showing the use of removable "VELCRO" hook and loop fastener unions, the enveloping elastic yielding bottom panty, as well as a dotted line soft pad, pressed by the strap thereabove and modelled onto the underlying body area, to stabilise the vertebral segment in its correct curvature preventing congenital alterations of the spine, as well as muscular disorders causing pain and vertigo to the pregnant woman;

FIG. 2a is a schematic sectional view along line a—a of FIG. 2, showing the cross section of the pad modelled to the body configuration by means of the pressing action of the backed strap thereover;

DETAILED DESCRIPTION OF THE INVENTION

Figure 1:
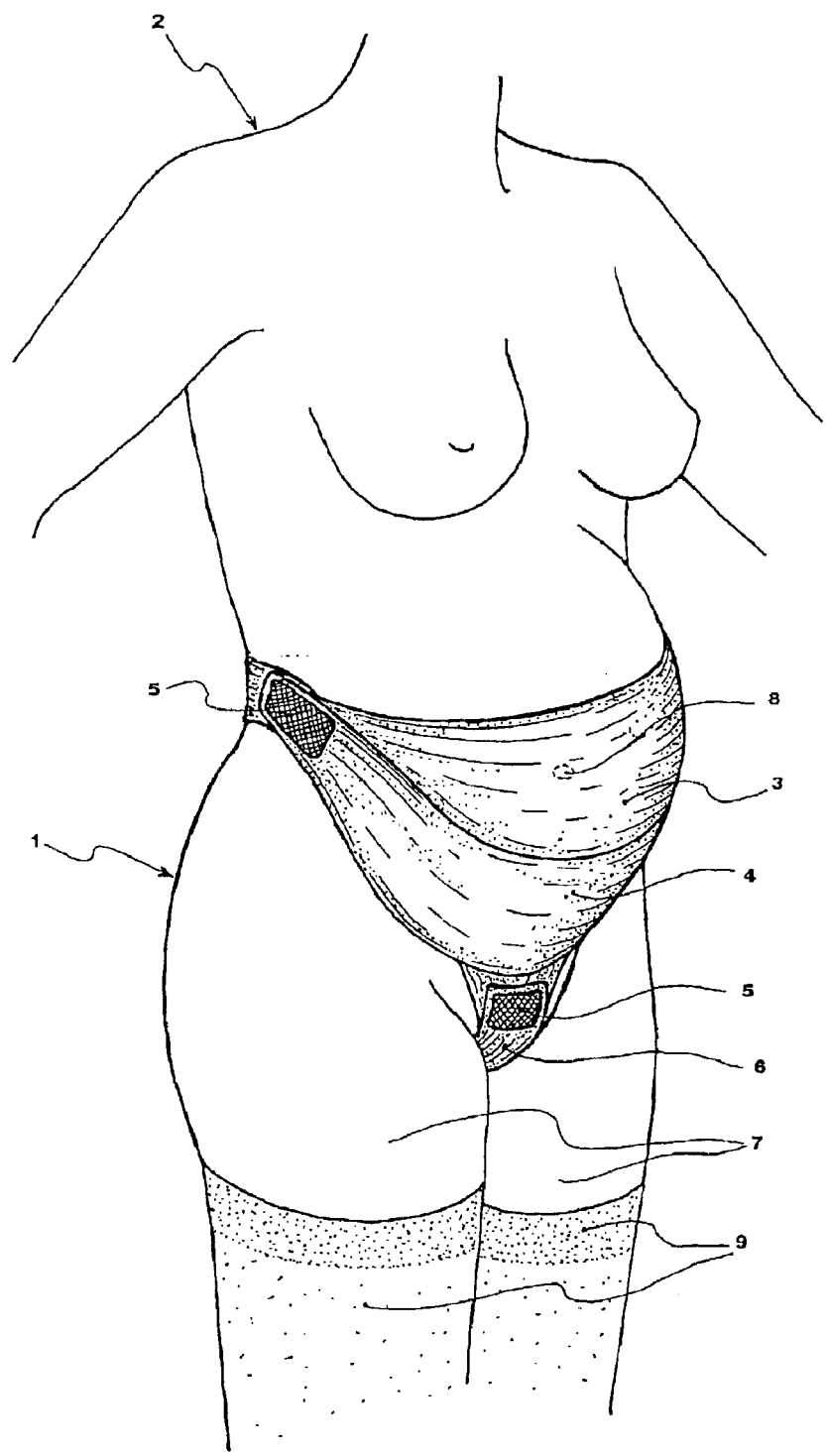
FIG. 1 is a schematic isometric perspective view of the abdominal suspensor of the present invention, showing the front portion of the pregnant abdomen enveloped by two straps, a bottom backed-structure for providing a supporting function and a thin yielding elastic structure for enveloping the entire abdominal wall, said view also showing the removable bottom band for the opening and the closing, as well as the panty enveloping the buttocks and the thighs near the groin, and, also, "VELCRO" hook and loop fastener straps for adjusting the removable unions with simple strapping actions.

In the Figs., corresponding or equivalent parts are identified by the same reference numbers for the sake of simplicity.

In the Figs., moreover, for the sake of overall clarity, the composite structures of the protector are not illustrated, and hence not described in the already known fabric composition thereof. Thus, e.g., the means for coupling the elastic stockings to the bottom edge of the panty, as well as the conductive yarn incorporated in the fabric for an electrical continuity and also the optical fibers, and the optical fiber sensors and the protective small rubber disks glued thereon are not shown nor described. Likewise, the electromedical comfort ware and the devices for the electronic monitoring devices for sensing the regularity of the fetal development in the uterus of the pregnant woman are not depicted nor shown in detail; and likewise, the battery generators and the radiofrequency transmitters for the telemetering irregular values of the monitored data, as well as the circuit details of such automation are not depicted or described, since they may be carried out in the same manner, as is well known in the art.

In the attached drawings element 1 is the abdominal suspensor of a backed structure enveloping and supporting the weight of the abdomen of the pregnant woman 2 through the structurally backed bottom strap 4, which is piece-formed to the yielding elastic top strap 3 which can contain preset conductive yarns throughout the structure of the fabric for enveloping and covering the entire abdominal wall above the navel 8. The composite structure backed bottom strap 4 joins, through the "VELCRO" hook and loop fastener strap 5, a removable connecting bottom band 6, advantageously allowing the tear-off opening and closing of the latter to the former.

The supporting band and bottom strap 4 joins, by means of the "VELCRO" hook and loop fastener straps 5 and with the right tensional adjustment, the backed strap 12, and the latter envelops and covers the sacrolumbar area with a shape suitable to be integrally fixed to the backed vertical strap 10, which joins at the groin to the band 6 by means of a fixed stitch or another type of fixed connection. The structural backed straps 4, 12, and 10 are piece-formed to the panty 7, which envelops the buttocks and the top ends of the legs 9 of the pregnant woman 2.

The backed sacrolumbar strap 12 in its closed position presses a pad 11 of a soft material to be modelled onto the underlying body area (see. FIG. 2a, sect. a—a) in order to stabilise this segment of the lumbar vertebrae in its correct curvature, thus preventing congenital alterations of the spine 17, as well as muscular disorders causing pain and vertigo to the pregnant woman 2. Upon wearing of the bottom abdominal suspensor 1, the pregnant woman 2 joins, with the connecting actions 13 and 14, the various structural supporting straps, which join together to form the bottom portion of the protector of the present invention.

Figure 3:
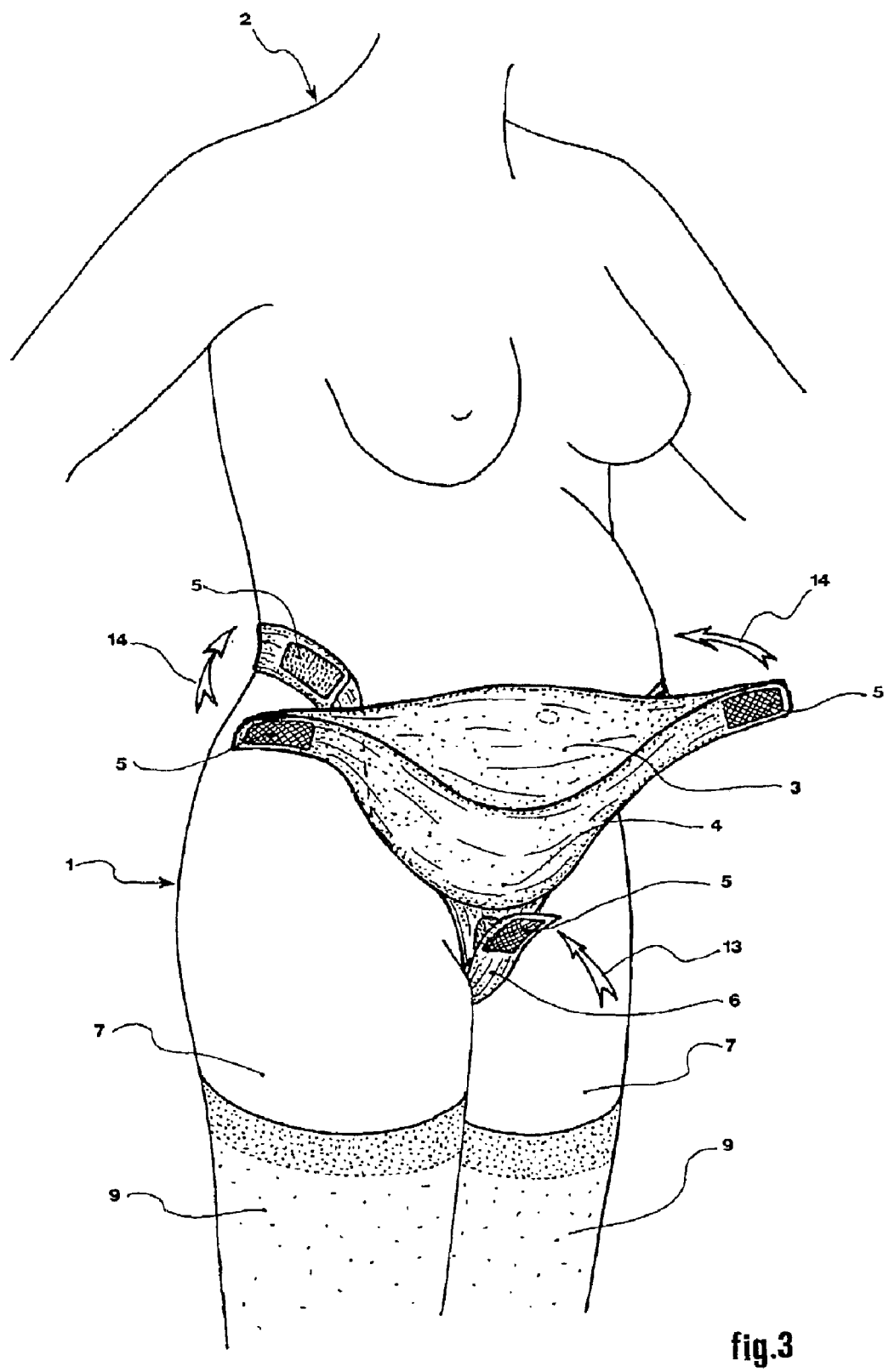
FIG. 3 is a schematic isometric perspective view of the abdominal suspensor shown in the front portion thereof with the structural straps and the underlying inguinal band, all in an opened position and unrestrained from the "VELCRO" hook and loop fastener areas, said view also showing the direction arrows for closing and adjusting the supporting device to the pregnant woman's need.
Figure 3A:
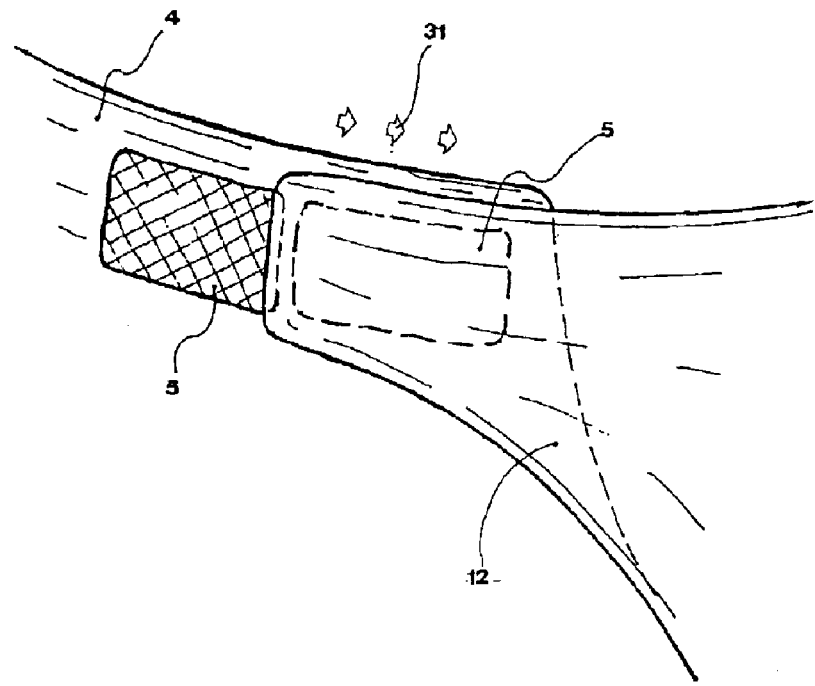
FIG. 3a is a schematic front view of the "VELCRO" hook and loop fastener union of two portions of the abdominal suspensor in a substantially medium adjustment position corresponding to the pregnancy period, i.e., the second half of gestation.
Figure 3B:
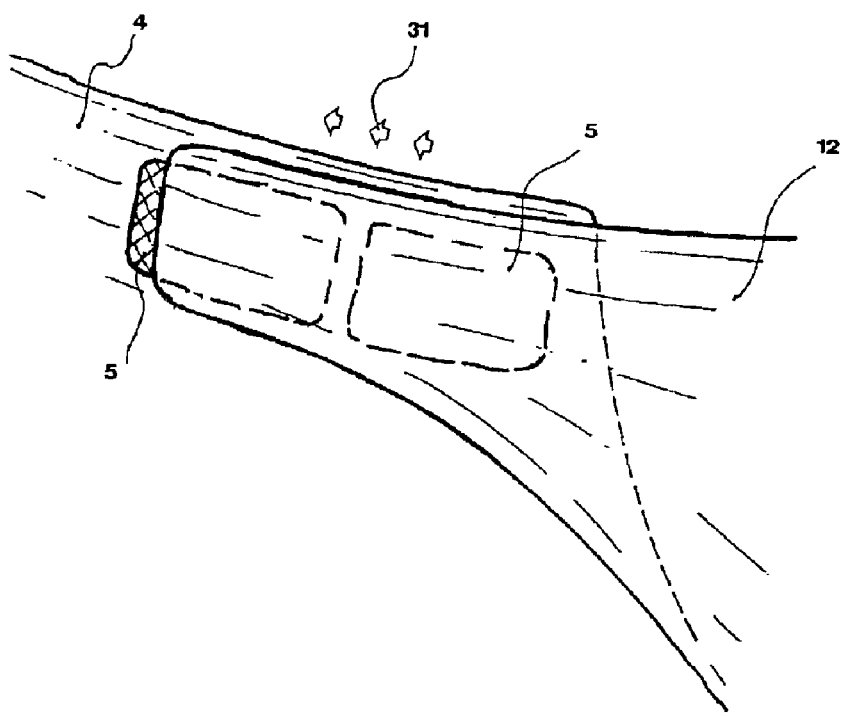
FIG. 3b is a schematic front view of a "VELCRO" hook and loop fastener union of two structural portions of the abdominal suspensor in a substantially tight adjustment position in correspondence with the pregnancy period, i.e., the first half of gestation.
Figure 4:
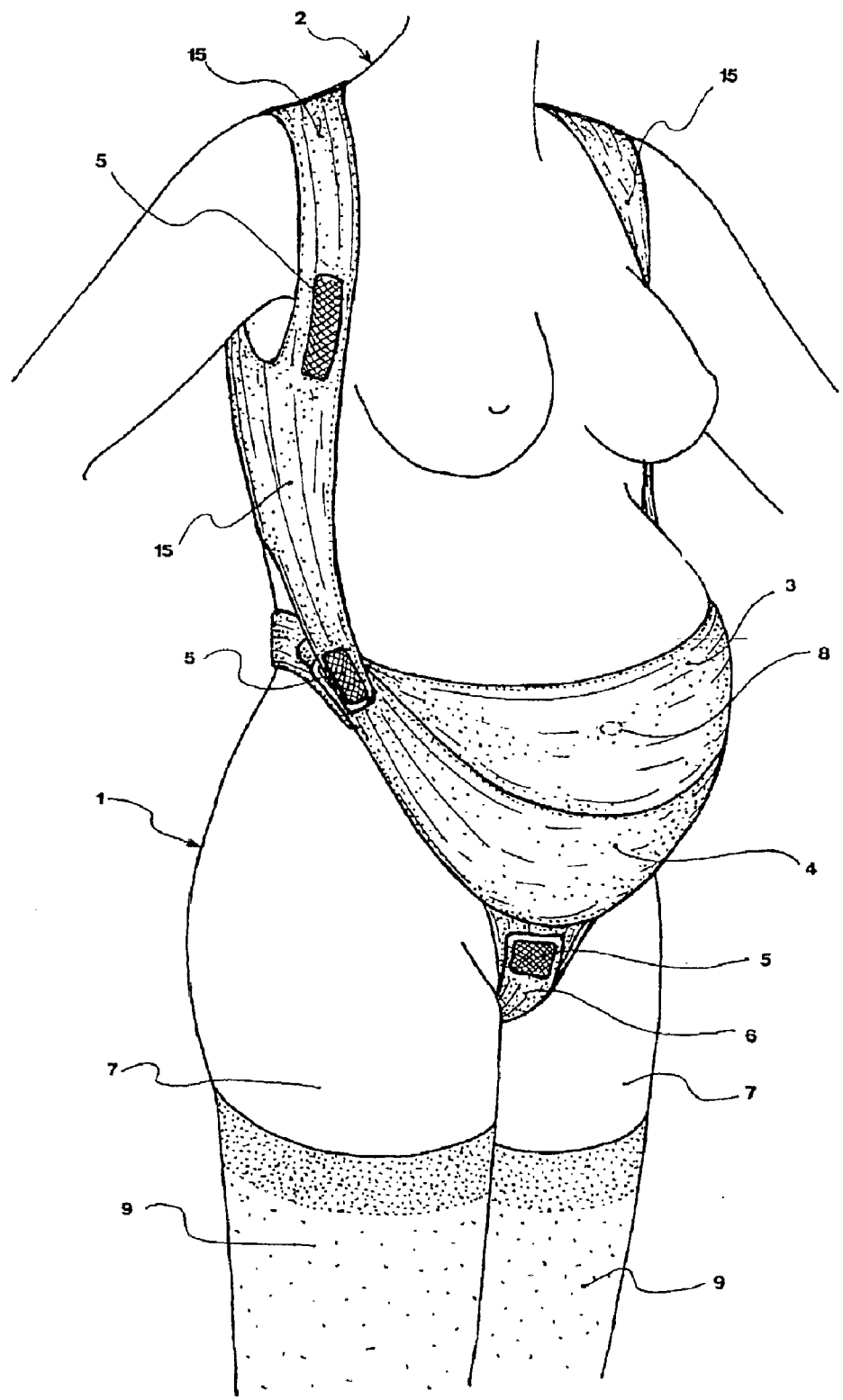
FIG. 4 is a schematic isometric perspective view of the dorsal and abdominal protector shown in a front portion thereof, said view also showing the "VELCRO" hook and loop fastener union of the bottom abdominal suspensor to the top dorsal bodice through the anterolateral straps onto which the 'Velcro' straps are provided.
Figure 5:
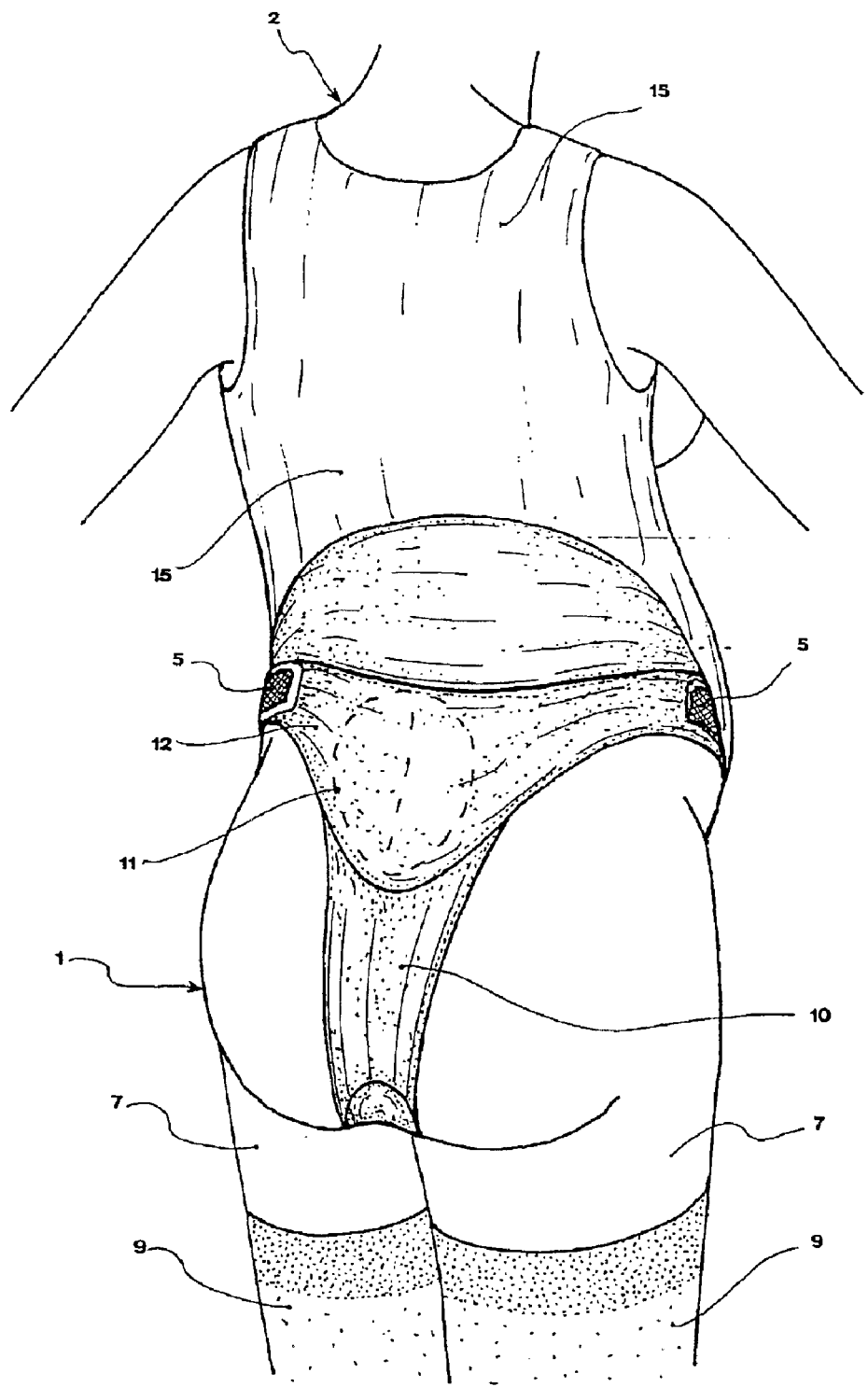
FIG. 5 is a schematic isometric perspective view of the dorsal and abdominal protector shown in the rear portion thereof, with backed straps enveloping the bottom area of the sacral spine to extend bottomwise of the inguinal band and, also, to extend topwise onto the iliac crestae. The top dorsal bodice loosely envelops the back and shoulders, said view also showing the enveloping bottom panty and the line of the pad substantially stabilising the segment of the lumbar vertebrae.
Figure 6:
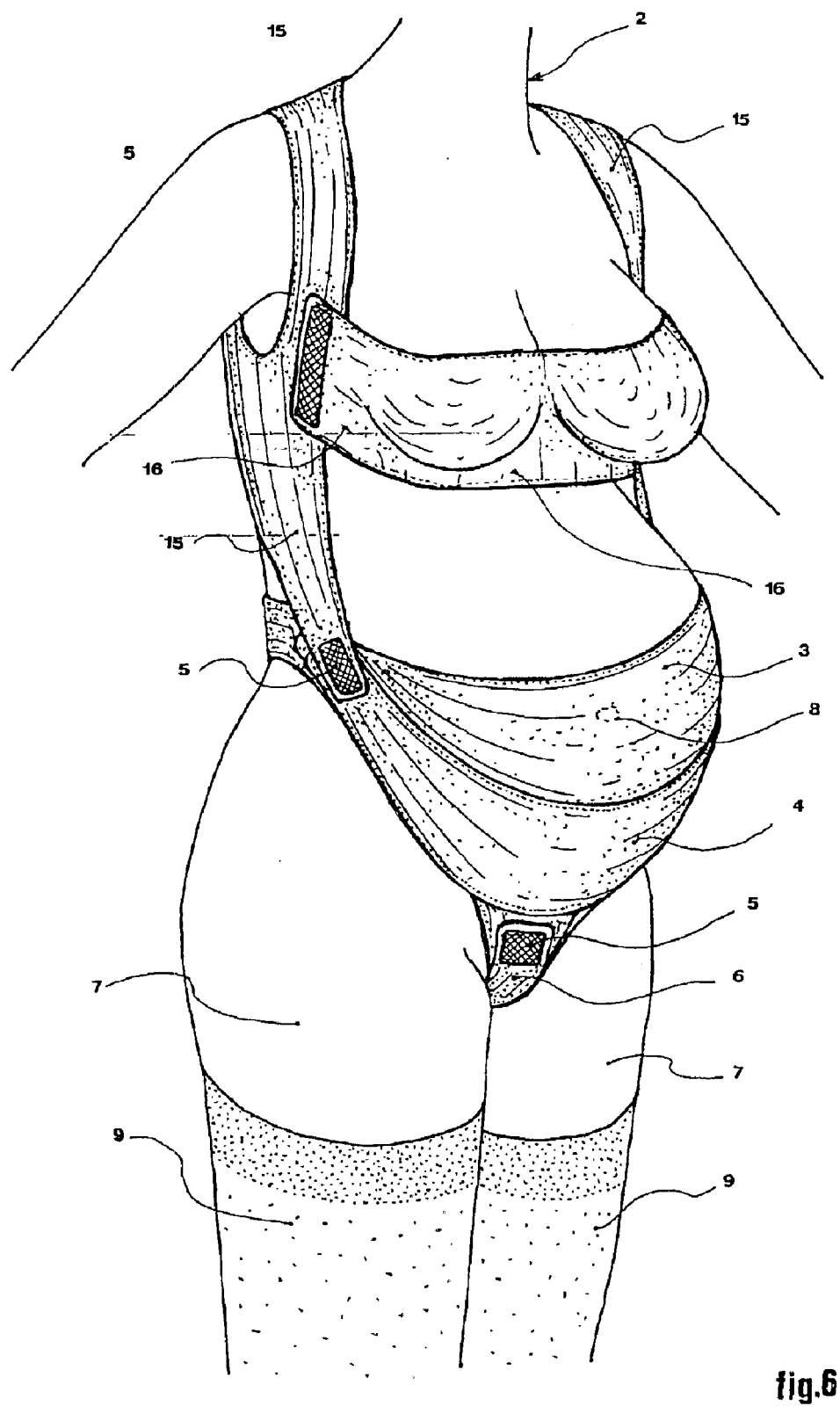
FIG. 6 is a schematic isometric perspective view of the dorsal and abdominal protector shown in the front portion thereof, similar to FIG. 4 with the addition of a bra strap advantageously coupled with "VELCRO" straps to the anterolateral straps of the supporting backed structure dorsal bodice.
Figure 7:
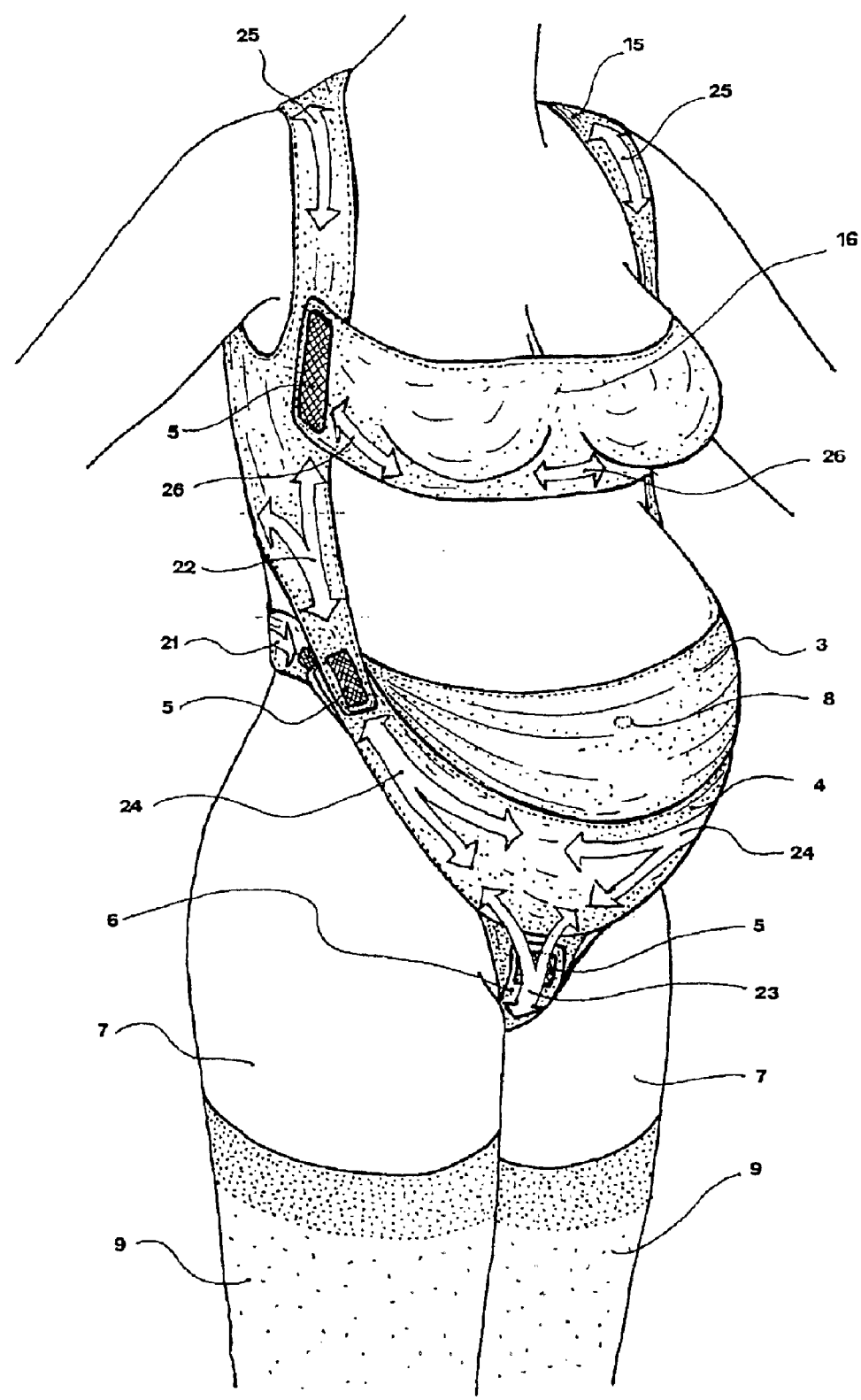
FIG. 7 is a schematic isometric perspective view of the dorsal and abdominal protector shown in the front portion thereof, analogous to FIG. 6, with the addition of the supporting vector forces between the bottom abdominal suspensor and the top dorsal bodice, said view also showing the transversal vector forces of the bra strap coupled to the anterolateral straps tensionally joining the various structural portions.
Figure 8:
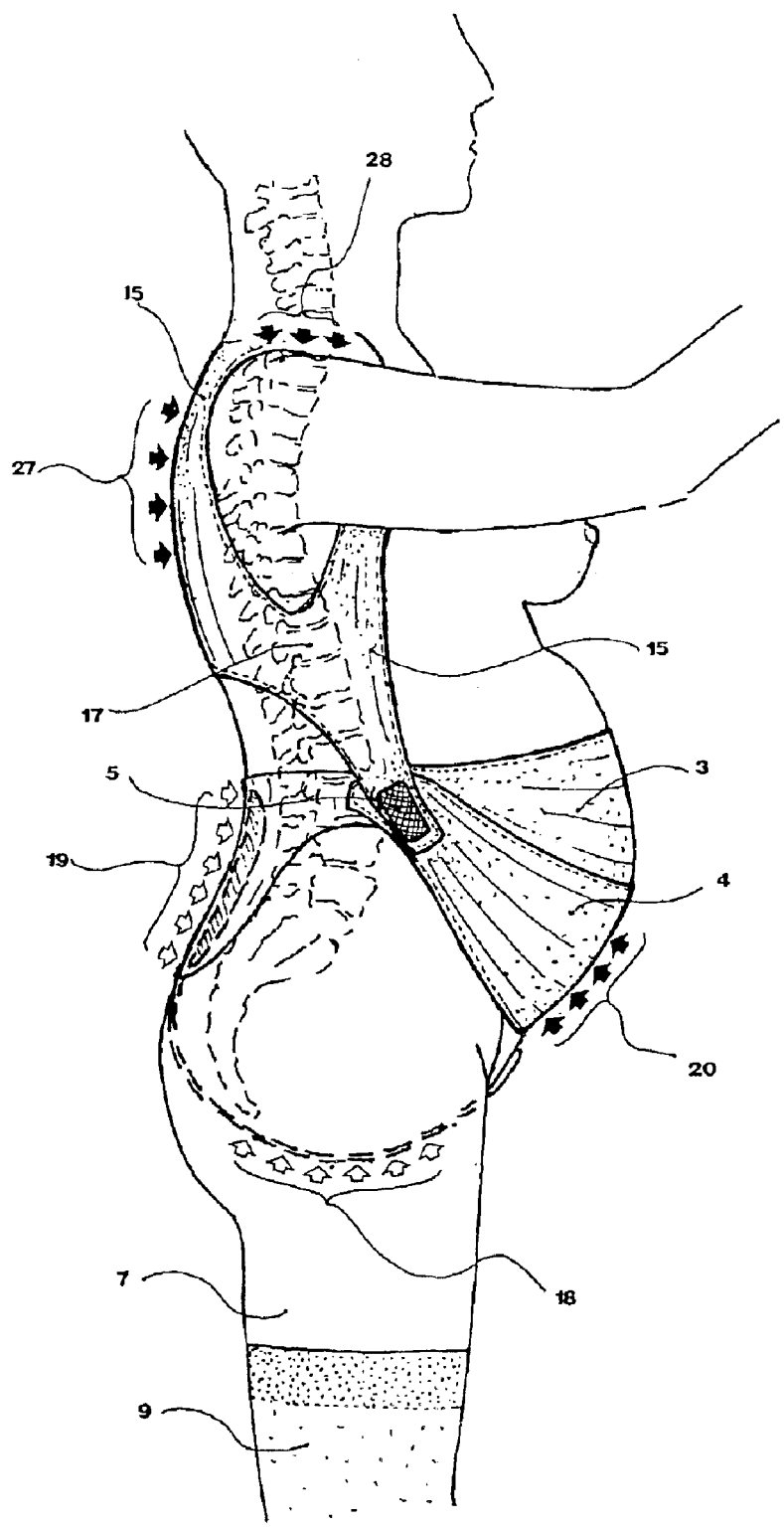
FIG. 8 is a schematic side view showing, with hatching, the spine, extending with its curvatures from the head to the pelvis of the pregnant woman and the resulting forces generated from the structural union of the abdominal suspensor, the dorsal bodice, and the shoulder girdle, according to the present invention.
Figure 9:
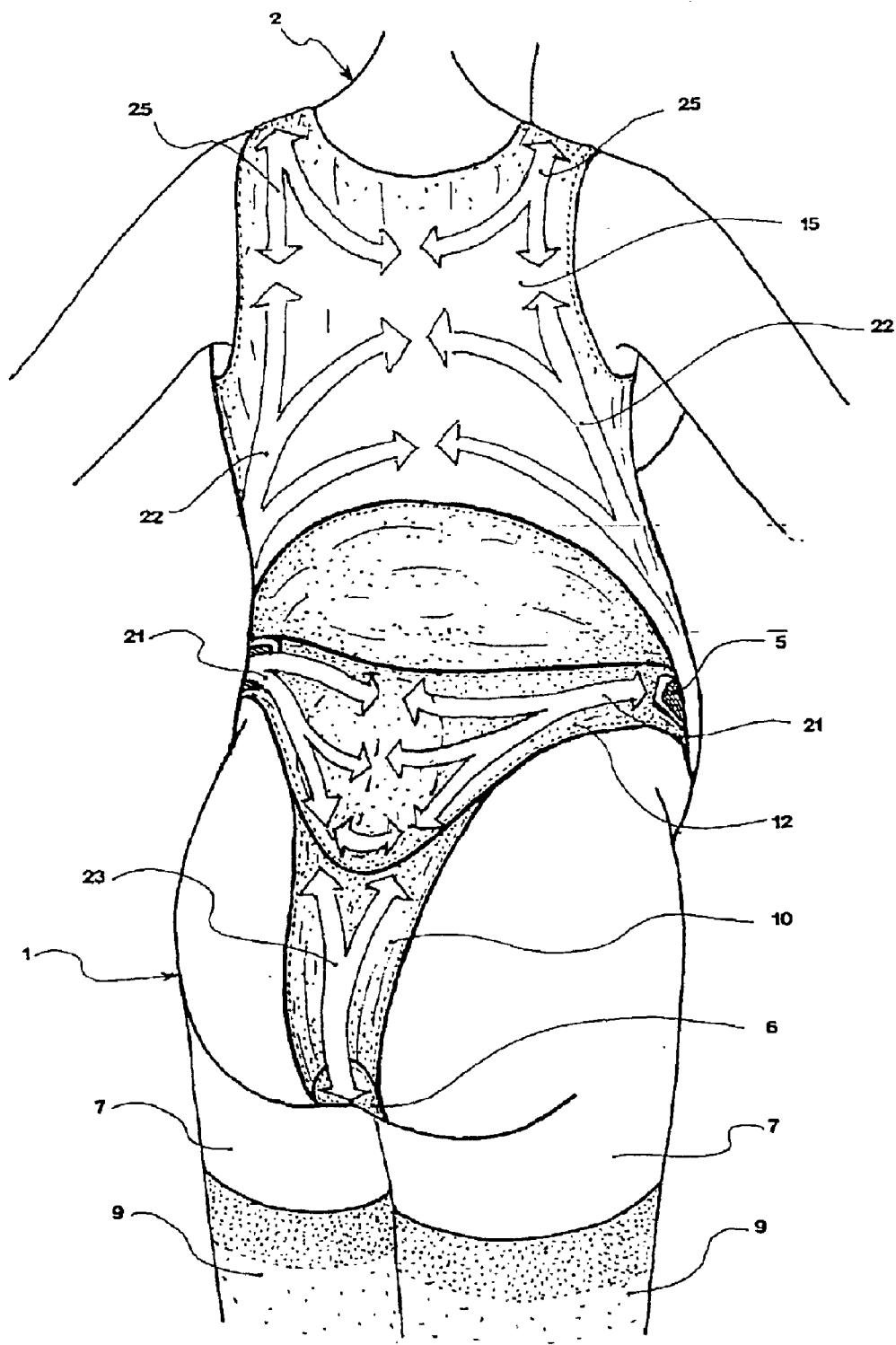
FIG. 9 is a schematic isometric perspective view of the dorsal and abdominal protector shown in the rear portion thereof with the supporting vector forces between the bottom abdominal suspensor and the top dorsal bodice.
Figure 10B:
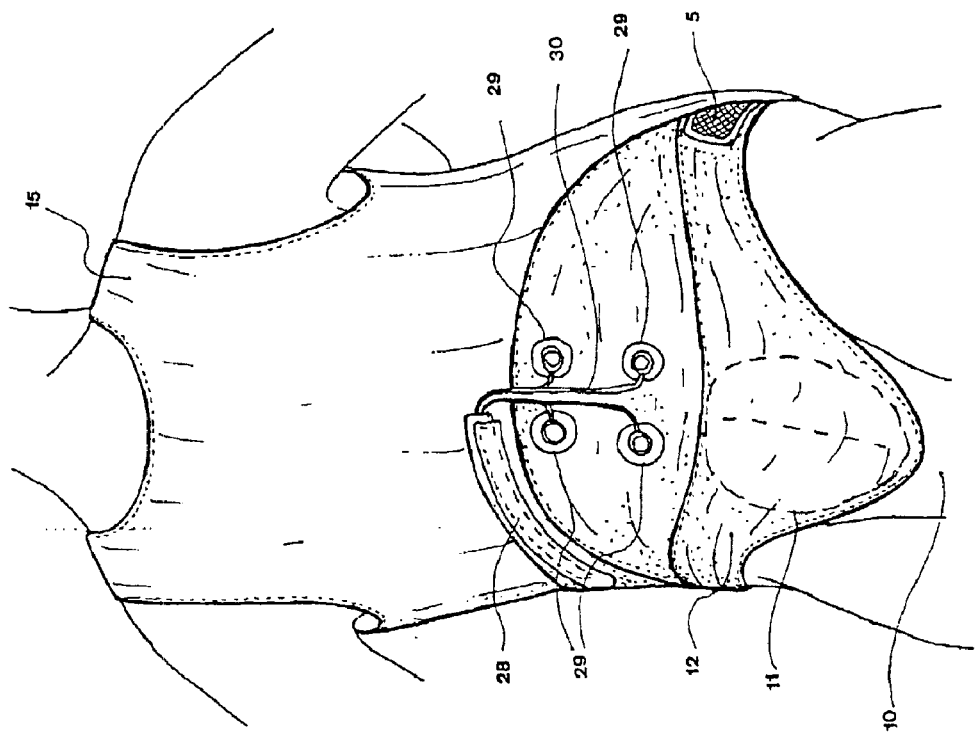
FIG. 10b is a schematic isometric perspective view of the rear portion of the dorsal and abdominal protector, associated to therapeutical devices which are in direct contact with the pregnant woman's skin, preferably in the dorsal area thereof.
Figure 10A:
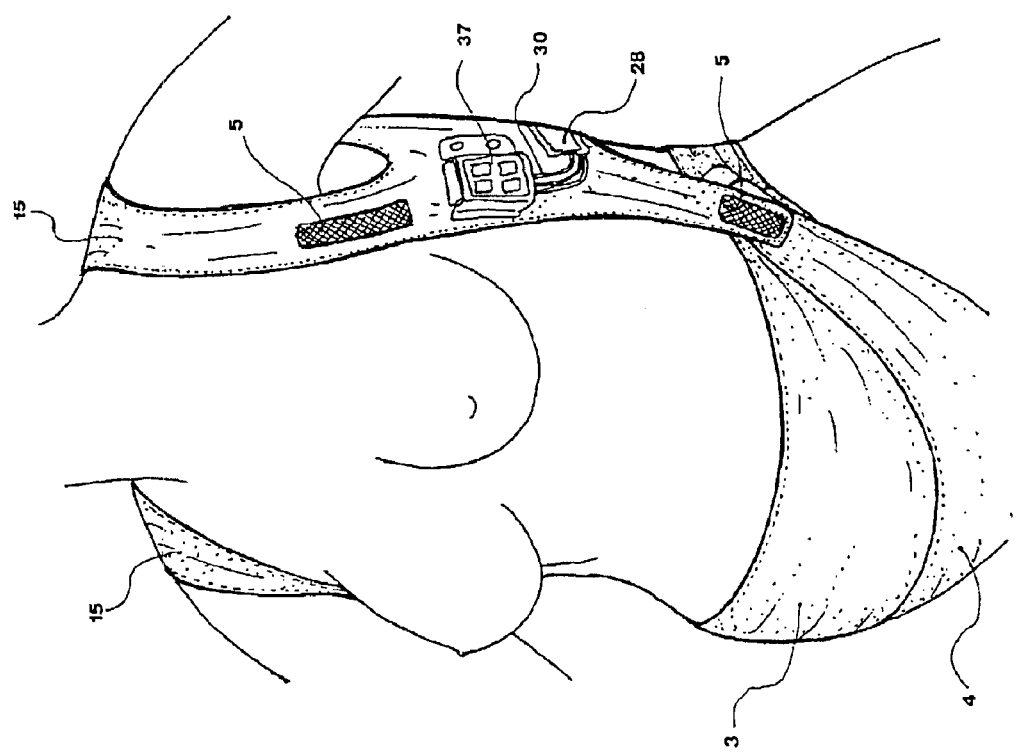
FIG. 10a is a schematic isometric perspective view of the dorsal and abdominal protector, and anterolateral strap associated with a fetal monitoring instrument containing a reading display for sensing, in real time, information on the foetal heart sounds and the prenatal uterine contractions, said view also showing the cables exiting from the monitoring instrument, to be advantageously connected to the electrical conductivity of the composite fabric of the former.

The "VELCRO" hook and loop fastener straps 5, with tear-off opening and closing, allow a ready and easy wearability adjustment in the union of the straps 4 and 12, according to the arrows 31 in accordance with the gestational period (see FIGS. 3a, 3b).

The top dorsal bodice 15, advantageously piece-formed for ready wearability, topwise envelops in an extended development both the shoulders and the dorsal portion to descend in a modelling of a suitable shape with two anterolateral straps, advantageously having "VELCRO" hook and loop fastener straps 5 for the removable couplings of both straps to the bottom abdominal suspensor 1 and the bra 16.

The vector forces 23, 21 and 24 supporting the pregnant abdomen of the abdominal suspensor 1 is transmitted and substantially compensated for and balanced by the vector forces 22 and 25 of the dorsal bodice 15, which protects the spine 17 supporting the weight of the pregnant abdomen on both shoulders through the loosely adjustable structural union between the abdominal suspensor 1 and the dorsal bodice 15. The transversal vector force 26 of the bra 16 is compensated for and balanced by the supporting vector forces 25 burdening the shoulder girdle, onto which substantially the entire weight of the pregnant abdomen of the pregnant woman 2 is discharged. The resulting supporting forces 20 of the pregnant abdomen, through the backed strap 4, are counterbalanced by the resulting forces 19 and 18, bringing the abdomen upwards in order to activate the backing off of the body barycentre allowed by the significant reduction of the gravitational load onto the abdomen itself by means of the resulting supporting back 27 and shoulder girdle of the shoulders 38.

The apparatus 37 pre-set to display foetal monitorings receives the sensed data and sends the processed data via the conductor cables 30, penetrating in electrical continuity along the protected strap 28 to join the conductive fibers of the composite fabric of the dorsal and abdominal protector of the present invention. The electrostimulation disks 29 for therapeutic use are directly positioned on the skin and fed with electric or electromagnetic stimulation waves via the cables 30, penetrating along the protected strap 28 to the generator, preferably a battery generator, positioned anywhere on the protector structure.

Obviously, the invention disclosed above is not limited to the embodiments of this protective structure for pregnant women, which is disclosed herein by way of example but rather it encompasses all the variants hereof derived from the same principle and which may differ only in technically equivalent solutions.

What is claimed is:

1. A dorsal and abdominal protector for supporting the abdomen of a pregnant woman which comprises:
    a dorsal bodice;
    a bra adjustably anchored to the dorsal bodice;
    a structured abdominal suspension strap adapted to contain and support the belly, said abdominal suspension strap being adjustably connected to said dorsal bodice by connecting straps; and
    connectors for adjusting the tension of the connecting straps.

2. A support structure for supporting body parts of a pregnant female which comprises:
    an abdominal suspensor adapted to support and contain the abdomen, said abdominal suspensor provided with abdominal side straps and a vaginal strap;
    a back strap provided with lateral back side straps and a back vertical strap, said back strap extending to support the back at the waist with the lateral back side straps adjustably connected to the abdominal side straps and the back vertical strap adjustably connected to the vaginal strap; and
    a top dorsal bodice enveloping the shoulders and extending from the shoulders laterally and separately along the body to adjustably connect with the abdominal suspensor at the waist.

3. The support structure of claim 2, wherein a bra for accommodating the breasts of the female is adjustably connected to the lateral extensions of the top dorsal bodice.

4. The support structure of claim 2, wherein an elastic panty and elastic stocking are operatively associated with the structure.

5. The support structure of claim 1, wherein the connectors are hook and loop fasteners.

6. The support structure of claim 2 wherein pads are positioned between said support structure and the body parts they are supporting.

7. The support structure of claim 2, wherein electronic fetal monitoring devices are operatively associated with said support structure for monitoring fetal activity.

8. The dorsal and abdominal protector of claim 1, wherein, when connected together, the dorsal bodice and abdominal protector form a single garment.

9. The dorsal and abdominal protector of claim 1, wherein the surface of the connecting straps which contact body parts is made of a thin permeable fabric adapted to protect the body parts.

10. A method of supporting the abdomen of a pregnant female which comprises:
    supporting and containing the abdomen with an abdominal suspensor, said abdominal suspensor containing abdominal side straps and a vaginal strap;
    providing a back strap containing lateral back side straps and a back vertical strap, said back strap extending to support the back at the waist with the lateral back side straps adjustably connected to the abdominal side straps and the back vertical strap adjustably connected to the vaginal strap; and
    adjustably connecting a top bodice, which envelops the shoulders and extends from the shoulder laterally, and separately along the body, with the abdominal suspensor, at the waist.

11. The method of claim 10, which further comprised adjustably attaching a bra, which accommodates the breasts, to the lateral extensions of the top dorsal bodice.

* * * * *